(12) United States Patent
Modi

(10) Patent No.: US 6,290,987 B1
(45) Date of Patent: *Sep. 18, 2001

(54) MIXED LIPOSOME PHARMACEUTICAL FORMULATION WITH AMPHIPHILES AND PHOSPHOLIPIDS

(75) Inventor: Pankaj Modi, Ancaster (CA)

(73) Assignee: Generex Pharmaceuticals, Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/391,664

(22) Filed: Sep. 7, 1999

Related U.S. Application Data

(63) Continuation-in-part of application No. 09/161,447, filed on Sep. 27, 1998, now Pat. No. 6,193,997.

(51) Int. Cl.[7] .................................................. A61K 9/127
(52) U.S. Cl. .................... 424/450; 424/400; 424/434; 424/464; 424/45; 424/46; 424/184.1; 424/198.1; 424/130.1; 424/725; 514/2
(58) Field of Search ........................... 424/45, 46, 195.1, 424/450, 400, 434, 464, 184.1, 198.1, 130.1, 725; 514/2

(56) References Cited

U.S. PATENT DOCUMENTS

| | | |
|---|---|---|
| 4,614,730 | 9/1986 | Hansen et al. . |
| 4,708,861 | 11/1987 | Popescu et al. . |
| 4,772,471 | 9/1988 | Vanlerberghe et al. . |
| 4,830,857 | 5/1989 | Handjani et al. . |
| 4,839,111 * | 6/1989 | Huang . |
| 4,900,730 | 2/1990 | Miyauchi . |
| 4,921,757 | 5/1990 | Wheatley et al. . |
| 5,147,723 | 9/1992 | Wallach . |
| 5,230,884 | 7/1993 | Evans et al. . |
| 5,234,767 | 8/1993 | Wallach . |
| 5,260,065 | 11/1993 | Mathur et al. . |
| 5,292,499 | 3/1994 | Evans et al. . |
| 5,306,483 * | 4/1994 | Mautone . |
| 5,376,646 | 12/1994 | Pittrof et al. . |
| 5,514,670 | 5/1996 | Friedman et al. . |
| 5,591,713 | 1/1997 | Igari et al. . |
| 5,643,600 | 7/1997 | Mathur . |
| 5,653,987 | 8/1997 | Modi et al. . |
| 5,665,700 | 9/1997 | Cho et al. . |
| 5,690,954 | 11/1997 | Illum . |
| 6,017,545 * | 1/2000 | Modi . |

FOREIGN PATENT DOCUMENTS

| | | |
|---|---|---|
| 0 200 383 | 12/1986 | (EP) . |
| 0 272 097 | 6/1988 | (EP) . |
| 0 475 160 | 3/1992 | (EP) . |
| 96 36352 | 11/1996 | (WO) . |
| 99 40932 | 8/1999 | (WO) . |

OTHER PUBLICATIONS

Kohler, D. (1993). Systemic Therapy with Aerosols. In: Aerosols in Medicine (Morén et al eds), Elsevier Science Publishers, pp. 303–319.*

Patton et al. (1992). Advanced Drug Delivery Reviews, vol. 8, pp. 179–196.*

* cited by examiner

*Primary Examiner*—Raj Bawa
(74) *Attorney, Agent, or Firm*—Debra Z. Anderson; Eckert Seamans Cherin & Mellott, LLC

(57) ABSTRACT

A mixed liposome pharmaceutical formulation with multilamellar vesicles is provided. The formulation comprises a pharmaceutical agent, water, an alkali metal alkyl sulfate, at least one membrane mimetic amphiphile, and at least one phospholipid. When aerosol delivery is intended, the formulation also comprises a propellant and a phenol. A metered dose dispenser containing the formulation, as well as a method of administering the formulation, are also provided.

34 Claims, No Drawings

MIXED LIPOSOME PHARMACEUTICAL FORMULATION WITH AMPHIPHILES AND PHOSPHOLIPIDS

The present application is a continuation-in-part of application Ser. No. 09/161,447, filed Sep. 27, 1998, now U.S. Pat. No. 6,193,997, issued Feb. 27, 2001.

FIELD OF THE INVENTION

The present invention relates to an improved delivery system for the administration of large-molecule pharmaceuticals, e.g. peptidic drugs, vaccines and hormones. In particular it relates to pharmaceuticals which may be administered through the oral and nasal membranes, or by pulmonary access. One method of administration is by means of an aerosol into the mouth, for buccal or pulmonary application.

BACKGROUND OF THE INVENTION

New methods of delivering large macromolecules (proteins and peptides) continue to be sought. One of the avenues investigated concerns the use of membrane-mimetic amphiphiles. A study of membrane-mimetic amphiphiles extends back to the first decade of the 20th century. Experiments using physical and chemical methods have shown that such molecules assume preferred arrays in the presence of water. Formation of these arrays, which includes micelles, monolayers and bimolecular layers is driven by the need of the polar head groups, which may be ionogenic or not, to associate with water, and the need of the polar hydrophobic tails to be excluded from water, (Small, D; Handbook of Lipid Research, vol. 4, 1986; Tanford, J: The Hydrophobic Effect, John Wiley & Sons, 1980; Fendler, J. Membrane Chemistry, 1982). Exactly which type of structure is assumed depends on upon the nature of the amphiphile, its concentration, the presence of other amphiphiles, temperature and the presence of salts and other solutes in the aqueous phase.

Membrane-mimetic amphiphiles include molecules that are insoluble in water but can take up water, and molecules that have appreciable solubility in water under limiting conditions. The former amphiphiles do not form molecularly disperse solutions in water but may swell considerably with water to form lamellar phases.

The latter amphiphiles can, at some temperatures, form solutions of dispersed monomers in water and often undergo the following sequence as the concentration in water is increased: monomeric solution to micellar solution. The manufacture of non-phospholipid liposomes, depends on the manipulation of environmental variables (e.g. temperature, hydration and composition) in an appropriate temporal sequence so as to cause non-phospholipid amphiphiles to form liposomal structures.

Gebicki et al. (Nature, 243, 232, 1973: Chem. Phys. Lipids, 16, 142, 1976; Biochem. Biophys. Res. Commun. 80, 704, 1978; Biochemistry, 17, 3759, 1978) demonstrated the formation of water containing vesicles enclosed by oleic acid. Others, as disclosed for example in U.S. Pat. Nos. 4,772,471 and 4,830,857, and in J. Microencapsul. 4, 321, 1987, have made lipid vesicles from single tailed ether or esters derivatives of polyglycerol. These liposomes were found suitable for cosmetic products. Murakami et al (J. Am. Chem. Soc, 101, 4030, 1979; J. Am Oil Chem Soc. 66, 599, 1989) formed single compartment vesicles with one or more bilayer walls composed of cationic amphiphiles involving amino acid residues. Kaler et al (Science, 245, 1371, 1989) demonstrated that appropriate aqueous mixtures of single-tailed cationic and anionic surfactants spontaneously form single-walled vesicles, presumably via salt formation. Others have developed methods for manufacture of paucilamellar, non-phospholipid liposomes that can be formed from a variety of amphiphiles as well as from certain phospholipids. The liposomes have two or more membranes surrounding an amorphous core, each membrane being composed of amphiphile molecules in bilayer array. The core accounts for most of the vesicle volume and encapsulating substances.

The above-mentioned non-phospholipid based liposomes are mainly used for the delivery of moisturizers and cosmetic ingredients used topically or externally as creams or moisturizers. In some cases such liposomes may be used as an ointment for delivery of some pharmaceutical products. Many ingredients utilized in the above products have been found to be inadmissible in the human body and are not approved by the regulatory agencies around the world for the purpose of oral administration and as a vehicle for delivery of macromolecules (proteins and peptides) as life saving therapeutics. Furthermore, other non-phospholipid based liposomes have been developed for non-pharmaceutical applications, e.g. water-borne oil paints, surface cleansers, heavy duty industrial cleansers and skin-cleansing detergents.

Certain aspects of the present invention aims at the development of oral compositions consisting of mixture of certain non-phospholipid based membrane-mimetic amphiphiles (suitable and approved by the regulating agencies for oral formulation of human pharmaceutical products) in combination of specific phospholipids to form multilamellar liposomes which are very stable and are smaller than the pores of the gastrointestinal (GI) tract.

Relatively very little progress has been made in reaching the target of safe and effective oral formulations for peptides and proteins. The major barriers to developing oral formulations for proteins and peptides include poor intrinsic permeability, lumenal and cellular enzymatic degradation, rapid clearance, and chemical stability in the GI tract. Pharmaceutical approaches to address these barriers, which have been successful with traditional small, organic drug molecules, have not readily translated into effective peptide and protein formulations. Although the challenges are significant, the potential therapeutic benefits remain high especially in the field of diabetes treatment using insulin.

Researchers have explored various administration routes other than injection for proteins and peptides. These routes include administration through oral, intranasal, rectal, vaginal cavities for the effective delivery of large molecules. Out of the above four mentioned routes oral and nasal cavities have been of greatest interest. Both the oral and nasal membranes offer advantages over other routes of administration. For example, drugs administered through these membranes have a rapid onset of action, provide therapeutic plasma levels, avoid a first pass effect of hepatic metabolism, and avoid exposure of the drug to a hostile GI environment. Additional advantages include easy access to the membrane sites so that the drug can be applied, localized and removed easily. Further, there is a good potential for prolonged delivery of large molecules through these membranes.

The oral routes have received far more attention than have the other routes. The sublingual mucosa includes the membrane of ventral surface of the tongue and the floor of the mouth whereas the buccal mucosa constitutes the lining of the cheek. The sublingual mucosa is relatively permeable thus giving rapid absorption and acceptable bioavailability of many drugs. Further, the sublingual mucosa is convenient, acceptable and easily accessible. This route has been investigated clinically for the delivery of a substantial number of drugs.

Various mechanisms of action of penetration of large molecules using enhancers have been proposed.

These mechanisms of action, at least for protein and peptidic drugs include (1) reducing viscosity and/or elasticity of mucous layer, (2) facilitating transcellular transport by increasing the fluidity of the lipid bilayer of membranes, (3) facilitating paracellular transport by altering tight junction across the epithelial cell layer, (4) overcoming enzymatic barriers, and (5) increasing the thermodynamic activity of drugs (Critical Rev. 117–125, 1992).

Many penetration enhancers have been tested so far and some have been found effective in facilitating mucosal administration of large molecular drugs. However, hardly any penetration enhancing products have reached the market place. Reasons for this include lack of a satisfactory safety profile respecting irritation, lowering of the barrier function, and impairment of the mucocilliary clearance protective mechanism. It has been found that some of the popular penetration enhancers, especially those related to bile salts, and some protein solubilizing agents, impart an extremely bitter and unpleasant taste. This makes their use impossible for human consumption on a day to day basis. Several approaches were utilized to improve the taste of the bile salts based delivery systems, but none of them are commercially acceptable for human consumption to date. Approaches utilized include patches for buccal mucosa, bilayer tablets, controlled release tablets, liposome formulations, use of protease inhibitors, bucally administered film patch devices, and various polymer matrices. Further the problem is compounded because of the localized side effect of a patch which often results in severe tissue damage in the mouth.

SUMMARY OF THE INVENTION

Accordingly the present invention provides a mixed liposome pharmaceutical formulation with multilamellar vesicles, comprising a proteinic pharmaceutical agent, water, an alkali metal C8 to C22 alkyl sulphate in a concentration of from 1 to 10 wt./wt. % of the total formulation, at least one membrane-mimetic amphiphile and at least one phospholipid, wherein the membrane-mimetic amphiphile is selected from the group consisting of hyaluronic acid, pharmaceutically acceptable salts of hyaluronic acid, lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, gamma-linoleic acid, borage oil, evening of primrose oil, monoolein, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, trihydroxy-oxo-cholanylglycine and alkali metal salts thereof, octylphenoxypolythoxyethanol, polydecanol X-lauryl ether, polydecanol X-oleyl ether, wherein X is from 9 to 20, and combinations thereof, and wherein the phospholipid is selected from the group consisting of, phospholipid GLA (glycolic, lactic acid), phosphatidyl serine, phosphatidylethanolamine, inositolphosphatides, dioleoylphosphatidylethanolamine, sphingomyelin, ceramides, cephalin, triolein, unsaturated lecithin, saturated lecithin and lysolecithin, and combinations thereof, and wherein the amount of each membrane-mimetic amphiphile and phospholipid is present in a concentration of from 1 to 10 wt./wt. % of the total formulation, and the total concentration of membrane-mimetic amphiphiles and phospholipids is less than 50 wt./wt. % of the formulation.

Preferably the mixed liposome pharmaceutical formulation has a pH of between 6.0 and 7.0.

The preferred number of membrane mimetic amphiphiles are from 2 to 5.

The preferred number of phospholipids are from 1 to 4.

In one embodiment, the alkali metal C8 to C22 alkyl sulphate is sodium lauryl sulphate.

In a preferred embodiment at least one protease inhibitor is added to the formulation to inhibit degradation of the pharmaceutical agent by the action of proteolytic enzymes. Of the known protease inhibitors, most are effective at concentrations of from 1 to 3 wt./wt. % of the formulation.

Non-limiting examples of effective protease inhibitors are bacitracin, soyabean trypsin, aprotinin and bacitracin derivatives, e.g. bacitracin methylene disalicylate. Bacitracin is the most effective of those named when used in concentrations of from 1.5 to 2 wt./wt. %. Soyabean trypsin and aprotinin may be used in concentrations of about 1 to 2 wt./wt. % of the formulation.

In one embodiment, the membrane-mimetic amphiphile is selected from the group consisting of hyaluronic acid, pharmaceutically acceptable salts of hyaluronic acid and mixtures thereof, the concentration such absorption enhancing compound being from about 1 to about 5 wt./wt. %.

In another embodiment, suitable for delivery through oral mucosal membranes, the formulation contains sodium lauryl sulphate, and combinations selected from the group consisting of:

i) sodium salt of trihydroxy-oxo-cholanyl glycine, sphingomyelin and stearamide DEA;

ii) sodium salt of trihydroxy-oxo-cholanyl glycine and phospholipid GLA;

iii) ceramide and stearamidopropyl phosphatidyl PG-diammonium chloride;

iv) borage amidopropyl phosphatidyl PG-diammonium chloride and lecithin;

v) octylphenoxypolyethoxyethanol and saturated lecithin;

vi) sodium hyaluronate, polydecanol 9-lauryl ether, lecithin and evening of primrose oil; and vii) monoolein, saturated lecithin, sodium hyaluronate and evening of primrose oil.

In yet another embodiment, suitable for topical delivery transdermally, the formulation contains sodium lauryl sulphate and combinations selected from the group consisting of:

i) lecithin, sodium hyaluronate, glycolic acid and propylene glycol; and ii) sodium hyaluronate, sphingomyelin, glycolic acid and propylene glycol.

Preferably the lecithin is saturated lecithin.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic mounts of other compounds may be included in the formulation.

In one embodiment the antioxidant is selected from the group consisting of tocopherol, deteroxime mesylate, methyl paraben, ethyl paraben and ascorbic acid and mixtures thereof. A preferred antioxidant is tocopherol.

The formulation suitable for delivery through oral mucosal membranes may be in chewable form, in which case it will be necessary to add ingredients suitable for such form. Such ingredients include guar gum, powdered acacia, carrageenin, beeswax and xanthan gum.

Another aspect of the invention provides a pressurized container containing a propellant which is liquid under pressure and an intermediate formulation which comprises:

i) a proteinic pharmaceutical agent, ii) water, iii) an alkali metal C8 to C22 alkyl sulphate in a concentration of from 1 to 10 wt./wt. % of the total formulation, iv) at least one membrane-mimetic amphiphile and at least one phospholipid, wherein the membrane-mimetic amphiphile is selected from the group consisting of hyaluronic acid, pharmaceutically acceptable salts of hyaluronic acid, lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, gamma-linoleic acid, borage oil, evening of primrose oil, monoolein, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, trihydroxy-oxo-cholanylglycine and alkali metal salts thereof, octylphenoxypolythoxyethanol, polydecanol X-lauryl ether, polydecanol X-oleyl ether, wherein X is from 9 to 20, and combinations thereof, and wherein the phospholipid is selected from the group consisting of, phospholipid GLA (glycolic, lactic acid), phosphatidyl serine, phosphatidylethanolamine, inositolphosphatides, dioleoylphosphatidylethanolamine, sphingomyelin, ceramides, cephalin, triolein, unsaturated lecithin, saturated lecithin and lysolecithin, and combinations thereof, and wherein the amount of each membrane-mimetic amphiphile and phospholipid is present in a concentration of from 1 to 10 wt./wt. % of the total formulation, and the total concentration of membrane-mimetic amphiphiles and phospholipids is less than 50 wt./wt. % of the formulation, and v) a phenolic compound selected from the group consisting of phenol and methyl phenol in a concentration of from 1 to 10 wt./wt. % of the total formulation.

In a preferred embodiment, the propellant is selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof.

In another embodiment, the intermediate formulation also contains a compound selected from glycerin, polyglycerin and mixtures thereof in an amount of from 1–40 wt./wt. % of the intermediate formulation.

In a further embodiment, the weight ratio of intermediate formulation to propellant is from 5:95 to 25:75.

In one embodiment, the alkali metal C8 to C22 alkyl sulphate is in a concentration of from 2 to 8 wt./wt. % of the intermediate formulation.

In a further embodiment, the methyl phenol is m-cresol.

In another embodiment, the alkali metal C8 to C22 alkyl sulphate is sodium lauryl sulphate.

In yet another embodiment, the total concentration of membrane mimetic amphiphiles is from about 1 to about 25 wt./wt. %.

In yet another embodiment, the propellant is selected from the group consisting of tetrafluoroethane, tetrafluoropropane, dimethylfluoropropane, heptafluoropropane, dimethyl ether, n-butane and isobutane.

In a further embodiment, the weight ratio of intermediate formulation to propellant is from 5:95 to 25:75.

The present invention also provides a metered dose aerosol dispenser with the propellant and intermediate formulation therein.

The present invention also provides a method for administering aerosol pharmaceutical compositions of the present invention, by spraying a predetermined amount of the composition into the mouth with a metered dose spray device.

The present invention also provides a method for administration of a proteinic pharmaceutical agent in a buccal cavity of a human being by spraying into the cavity, without inhalation, from a metered dose spray dispenser, a predetermined amount of a mixture of the propellant and the intermediate formulation.

In one embodiment, the metered dose spray dispenser is vigorously shaken immediately prior to administration of the proteinic pharmaceutical agent.

The proteinic pharmaceutical agent may be selected from a wide variety of macromolecular agents, depending on the disorder being treated, generally with molecular weights greater than about 1,000 and especially between about 1,000 and 2,000,000. Pharmaceutical agents useful in the present invention include insulin, heparin, low molecular weight heparin, hirugen, hirulos, hirudine, interferons, interleukins, cytokines, mono and polyclonal antibodies, chemotherapeutic agents, vaccines, glycoproteins, bacterial toxoids, growth hormones, parathyroid hormone (PTH), calcitonins, insulin like growth factors (IGF), glucagon like peptides (GLP-1 and GLP-2), steroids and retinoids, injectable large molecule antibiotics, protein based thrombolytic compounds, platelet inhibitors, DNA, gene therapeutics, RNA and antisense oligonucleotides.

DETAILED DESCRIPTION OF PREFERRED EMBODIMENTS

When developing new pharmaceutical formulations, it is desirable to provide dosage forms suitable for administering proteinic and peptidic drugs to humans and animals through oral, nasal, pulmonary and transdermal mucosal routes and to allow easy accessibility to the sites of administration. Local absorption of macromolecular drugs is desirable over a prolonged period to maximize drug absorption. Furthermore, it is desirable to minimize tissue damage and provide acceptable tissue compatibility of the dosage form. It is preferable to provide systems which are pain free and easy to be administered with great flexibility, in order to gain high acceptance and compliance of any therapy by patients.

It has been found that macromolecular drugs may be administered in mixed liposomal formulations in which particle sizes (1 to 4 nm) are smaller than any pores of mucosal surfaces.

The present invention provides an improved method for delivery of macromolecular (high molecular weight) pharmaceutical agents, particularly through the skin or membranes in the nose, mouth, lungs, vagina or rectum. The preferred delivery is through oral and nasal cavities. Even more preferred is delivery into the buccal cavity using a metered dose dispenser. The pharmaceutical agents cover a wide spectrum of agents, including proteins, peptides, hormones, vaccines and drugs. The molecular weights of the macromolecular pharmaceutical agents are preferably above 1,000, especially between 1,000 and 2,000,000.

For example, hormones which may be administered with the present invention include human growth hormones, parathyroid hormones, follicular stimulating hormones, luteinizing hormones, androgens, oestrogens, prostoglandins, somatropins, gonadotropins, erythropoetin, interferons, interleukins, steroids and cytokines.

Vaccines which may be administered with the present invention include bacterial and viral vaccines such as vaccines for hepatitis A, hepatitis B, hepatitis C, influenza, tuberculosis, canary pox, chicken pox, measles, mumps, rubella, pneumonia, BCG, HIV, helicobector pylori and AIDS.

Bacterial toxoids which may be administered using the present invention include diphtheria, tetanus, pseudomonas and mycobacterium tuberculosis.

Examples of specific cardiovascular or thrombolytic agents include heparin, low molecular weight heparin, hirugen, hirulos and hirudine.

As will be understood, the concentration of the pharmaceutical agent is an amount sufficient to be effective in treating or preventing a disorder or to regulate a physiological condition in an animal or human. The concentration or amount of pharmaceutical agent administered will depend on the parameters determined for the agent and the method of administration, e.g. oral, nasal, transdermal, pulmonary. For example, nasal formulations tend to require much lower concentrations of some ingredients in order to avoid irritation or burning of the nasal passages. It is sometimes desirable to dilute an oral formulation up to 10–100 times in order to provide a suitable nasal formulation.

Preferred methods of forming mixed non-phospholipid membrane mimetic amphiphiles and phospholipid are based on the phase behaviour of lipid amphiphiles and phospholipids. Such methods use high turbulence or high shear methods of mixing, e.g. turbines or high velocity nozzles. For example, the membrane-mimetic amphiphiles may be injected at high velocity, e.g. through nozzles, into an aqueous phase of the phospholipid. Alternatively, the membrane mimetic amphiphiles and the phospholipids may be mixed in a mixing chamber into which the phospholipids are injected at high velocity through one or more nozzles and the membrane-mimetic amphiphiles are also injected at high velocity through one or more nozzles. Other ingredients, such as sodium C8 to C22 alkyl sulphate, protease inhibitors may be premixed with either the membrane-mimetic amphiphile or the phospholipid. The velocity and mixing of the two liquids depends in part on the viscosities of the materials and nozzle diameters, e.g. 10 to 15 m/s through 0.5 to 1.0 mm diameter nozzle apertures. Typically the ratio of the membrane-mimetic amphiphile aqueous solution to the phospholipid solution is about 5:1 to about 20:1 and the temperature of mixing is typically from about 10° C. to 20° C.

It may sometimes be necessary to heat the membrane-mimetic amphiphiles and other ingredients in order to yield a homogeneous aqueous solution prior to mixing with the phospholipids. The nature of the proteinic pharmaceutical may also dictate the temperature range at which mixing may take place. The temperature of mixing is typically room temperature or below, but may be higher than room temperature for certain formulations. The resulting formulation contains multi-lamellar liposomal vesicles. If the formulation has been heated during mixing, it is sometimes desirable to cool the mixture while still being mixed, in order to assist in the formation of the multi-lamellar vesicles.

Mixed multi-lamellar vesicles formed by the present process are very small in size, e.g. less than 10 nm, and are stable under most storage conditions.

Preferably, the membrane-mimetic amphiphile solution is injected into the phospholipid solution through tangentially placed nozzles in a small cylindrical mixing chamber. Preferably, one or two nozzles are used for the membrane-mimetic amphiphile solution and one or two alternating nozzles for the phospholipid solution. The two liquids are preferably delivered to the nozzles by flow-controlled positive displacement pumps.

Although the present invention has such wide applicability, the invention is described hereinafter with particular reference to insulin and its analogues, which are used for the treatment of diabetes.

In the case of insulin, which is intended for administration through nasal or oral cavities, an aqueous buffer solution may be made first by adding aqueous alkali metal C8 to C22 alkyl sulphate, e.g. sodium lauryl sulphate, to powdered insulin, and then stirring until the powder is dissolved and a clear solution is obtained. The buffer solution may also contain sodium salicylate. Typical concentrations of sodium salicylate and sodium lauryl sulphate in the aqueous solution are about 3 to 20 wt./wt. % of each compound in the solution. Typically, insulin is present in the solution in an amount which will give a concentration of about 2 to 4 wt./wt. % of the final formulation.

The buffer solution is then added to liquid which comprises a membrane-mimetic amphiphile or a phospholipid while mixing vigorously, to form multi-lamellar liposomal vesicles.

The membrane-mimetic amphiphile is selected from the group consisting of hyaluronic acid, pharmaceutically acceptable salts of hyaluronic acid, lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, gamma-linoleic acid, borage oil, evening of primrose oil, monoolein, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, trihydroxy-oxo-cholanylglycine and alkali metal salts thereof, octylphenoxypolythoxyethanol, polydecanol X-lauryl ether, polydecanol X-oleyl ether, wherein X is from 9 to 20, and combinations thereof. Preferably X is 9, 10 or 20.

The phospholipid is selected from the group consisting of phospholipid GLA, phosphatidyl serine, phosphatidylethanolamine, inositolphosphatides, dioleoylphosphatidylethanolamine, sphingomyelin, ceramides, cephalin, triolein, unsaturated lecithin, saturated lecithin and lysolecithin.

Each of the membrane-mimetic amphiphiles and phospholipids are present in a concentration of from 1 to 10 wt./wt. % of the total formulation.

Preferred salts of hyaluronic acid are alkali metal hyaluronates, alkaline earth hyaluronates and aluminium hyaluronate. The preferred salt is sodium hyaluronate. The preferred concentration of hyaluronic acid or pharmaceutically acceptable salts of hyaluronic acid is from 1 to 5 wt./wt. % of the total formulation. An even more preferred range is from 1.5 to 3.5 wt./wt. % of the total formulation.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic amounts of other compounds may be included in the formulation. Typical flavouring agents are menthol, sorbitol and fruit flavours.

The antioxidant may be selected from the group consisting of tocopherol, deteroxime mesylate, methyl paraben, ethyl paraben and ascorbic acid and mixtures thereof. A preferred antioxidant is tocopherol.

In a preferred embodiment at least one protease inhibitor is added to the formulation to inhibit degradation of the pharmaceutical agent by the action of proteolytic enzymes. Of the known protease inhibitors, most are effective at concentrations of from 1 to 3 wt./wt. % of the formulation.

Non-limiting examples of effective protease inhibitors are bacitracin, soyabean trypsin, aprotinin and bacitracin derivatives, e.g. bacitracin methylene disalicylate. Bacitracin is the most effective of those named when used in concentrations of from 1.5 to 2 wt./wt. %. Soyabean trypsin and aprotinin two may be used in concentrations of about 1 to 2 wt./wt. % of the formulation.

For insulin-containing and some other compositions, the composition may also contains at least one inorganic salt which helps to open channels in the membranes of the mouth or lungs, and may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

In general the size of the multi-lamellar liposomal vesicle particles is about from 1 to 10 nm, and preferably from 1 to 5 nm. Such a size distribution ensures effective absorption of the formulation, and therefore the pharmaceutical agent, through the membranes, for example the membranes in the oral and nasal cavities.

The specific concentrations of the essential ingredients can be determined by relatively straightforward experimentation. For absorption through the nasal and oral cavities, it is often desirable to increase, e.g. double or triple, the dosage which is normally required through injection of administration through the gastrointestinal tract.

As will be understood, the amount of each component of the formulation will vary depending on the pharmaceutical agent and the site of application.

For oral application, sodium C8 to C22 alkyl sulphate and sodium edetate are insufficient on their own and must be combined with at least one membrane-mimetic amphiphile and at least one phospholipid to promote the oral absorption of macromolecules to achieve therapeutic effects.

The oral formulations may be mixed with a suitable propellant and delivered with a suitable applicator.

Preferred formulations oral or nasal application have the following combinations, in addition to sodium lauryl sulphate:
 i) sodium salt of trihydroxy-oxo-cholanyl glycine, sphingomyelin and stearamide DEA;
 ii) sodium salt of trihydroxy-oxo-cholanyl glycine and phospholipid GLA;
 iii) phospholipid GLA, polydecanol 9-lauryl ether and octylphenoxyethoxyethanol;
 iv) ceramide and stearamidopropyl phosphatidyl PG-diammonium chloride;
 v) borage amidopropyl phosphatidyl PG-diammonium chloride and lecithin;
 vi) octylphenoxypolyethoxyethanol and saturated lecithin;
 vii) lecithin, evening of primrose oil and trihydroxy-oxo-cholanylglycine;
 viii) sodium hyaluronate, trihydroxy oxo-cholanylglycine, lecithin and evening of primrose oil; and
 ix) saturated lecithin, sodium hyaluronate, and evening of primrose oil.

Some preferred compositions for transdermal application have the following absorption enhancing compound combinations, in addition to sodium lauryl sulphate and sodium edetate: i) sodium hyaluronate, saturated lecithin, glycolic acid and propylene glycol; ii) sodium hyaluronate, sphingomyelin, glycolic acid and propylene glycol.

For topical applications, enhanced skin penetration can be obtained with a combination of glycolic lactic acid propylene glycol with the liposomes.

The therapeutic compositions of the present invention can be stored at room temperature or at cold temperature. Storage of proteinic drugs is preferable at a cold temperature, e.g. 4° C., to prevent degradation of the drugs and to extend their shelf life.

As indicated hereinbefore, generally, oral, pulmonary, transdermal and nasal are the favoured sites of the administration but the composition can be applied to the rectal and vaginal mucosa. According to the physiologically active peptide or protein used, the dosage form and the site of administration a specific administration method can be selected.

The composition of this invention is generally prepared as microfine multi-lamellar liposomal vesicle particles (1 to 10 nm or less) by the virtue of its preparation methods used and combinations suitable characteristics of the membrane mimetic amphiphiles and phospholipids.

Administration of the formulation is by methods generally known in the art. For oral and nasal application, sprays are preferable. Other methods include the use of drops, chewable tablets, chewable gum, suppositories, lotions and ointments. Utilization of atomizer or aerosol spray devices (metered dose inhalers or nebulizers) can be used to further reduce the particle size for effective inhalation from the nasal or oral cavity so the drug may successfully reach to the specific site, especially the lungs, and be absorbed.

It is also possible to utilize a drug delivery system such that an enteric coating is applied to the gelatin capsule to cause the micelles to be released only in the duodenum or in the proximity of the large intestine and not in the stomach.

As indicated hereinbefore, oral or pulmonary administration may be desirable. Preferably, the pharmaceutical is administered using a metered dose dispenser, in which the pharmaceutical formulation is delivered with a propellant.

To prepare an aerosol formulation, phenol and/or methyl cresol, e.g. m-cresol, may be added to stabilize the formulation and protect against bacterial growth. An isotonic agent such as glycerin may also be added. The formulation is then put into an aerosol dispenser and the dispenser charged with the propellant. The propellant, which is under pressure, is in liquid form in the dispenser. In the present invention, when the composition of the present invention is in a dispenser, the aqueous phase may be separated from the propellant phase. Preferably, however, the ratios of the ingredients are adjusted by simple experimentation so that the aqueous and propellant phases become one, i.e. there is one phase. If there are two phases, it is necessary to shake the dispenser prior to dispensing a portion of the contents, e.g. through a metered valve. The dispensed dose of pharmaceutical agent is propelled from the metered valve in a fine spray.

The preferred propellants are hydrogen-containing chlorofluorocarbons, hydrogen-containing fluorocarbons, dimethyl ether and diethyl ether. Even more preferred is hydrofluoroalkane (HFA) 134a (1,1,1,2 tetrafluoroethane).

A particular advantage with the use of metered dose dispensers is that the formulation can be delivered in a relatively precise dose, e.g. titratable to injection within 1 unit of insulin dose. The droplet size of the formulation preferably falls between 1–5 $\mu$m in order for droplets to penetrate buccal mucosa or to reach to the deep lung surface. Thus, the present invention is suitable for delivery of proteinic drugs such as insulin for the treatment of diabetes.

The pressurized dispenser also offer a wide dosing range and consistent dosing efficiency. With such a delivery, greater than about 95% of the dose may reach the target area. The smaller particle size (1–5 $\mu$m) obtained using pressurized dispensers also enhances dosing due to broader coverage within the lung cavity. In this situation, increased coverage can help more absorption of a drug like insulin. Furthermore, because these devices are self-contained, potential contamination is avoided.

The specific concentrations of the essential ingredients can be determined by relatively straightforward experimentation. It will be understood that the amounts of certain ingredients may need to be limited in order to avoid compositions which produce foam when sprayed rather than forming a fine spray. For absorption through the oral cavities, it is often desirable to increase, e.g. double or triple, the dosage which is normally required through injection or administration through the gastrointestinal tract.

As will be understood, the amount of each component of the formulation will vary depending on the pharmaceutical agent and the site of application.

Administration of the formulation into the buccal cavity is by spraying the formulation into the mouth, without inhalation, so that the droplets stay in the mouth rather than be drawn into the lungs.

The invention is illustrated by reference to the following examples.

EXAMPLE 1

26,000 units (1,000 mg) of insulin crystals were suspended in 150 mL 0.3M hydrochloric acid and the solution was stirred to dissolve the crystals completely. The pH was adjusted to 7.0 by neutralizing with 0.3M sodium hydroxide. The final volume was adjusted to 260 mL to give 100 units/mL insulin concentration.

To 10 mL of insulin solution, 50 mg of sodium lauryl sulphate was added and dissolved completely. In 50 mL of water, 50 mg trihydroxy-oxo-cholanylglycine and 50 mg polydecanol 20-oleyl ether were added and dissolved and then mixed with the insulin solution. This mixture was then sprayed under pressure into a 1 wt. % solution of phospholipid GLA to form mixed micelles. This procedure gave a mixed amphiphile insulin solution with 50 units/mL.

The structure of the mixed amphiphile insulin was examined under a light microscope and the particle size was analysed by laser light scattering. The average particle size was estimated to be about 2 to 10 nm.

In one set of tests, ten diabetic human volunteers who normally took insulin by injection three times a day, were studied. The volunteers were tested with insulin, taken orally. The volunteers fasted from midnight prior to the test, with no food being taken during the 4 hour study.

Each of the volunteers received 10 units insulin. In one test, the oral insulin was administered with a metered dose spray. In another test, the insulin was administered by injection. Blood glucose levels, in mmol/L, were monitored every 15–30 minutes by Bayer's Glucometer Elite.

The average results for the ten volunteers, of the trial were as follows:

TABLE I

| Time (minutes) | Oral Insulin (10 units) | Injection (10 units) |
| --- | --- | --- |
| 0 | 11.0 | 10.5 |
| 15 | 10.6 | 10.5 |
| 30 | 10.2 | 10.4 |
| 45 | 9.3 | 10.2 |
| 60 | 8.6 | 9.5 |
| 90 | 7.0 | 8.2 |
| 120 | 6.5 | 6.8 |
| 150 | 5.9 | 5.5 |
| 180 | 5.1 | 4.7 |

The results show that the oral insulin formulation, within the scope of the present invention, at an equivalent dosage, is comparable with the injected insulin.

EXAMPLE II

To 10 mL of the insulin solution prepared in Example I, 50 mg of sodium lauryl sulphate was added and dissolved completely. In 50 mL of water, 50 mg lauramidopropyl betain and 50 mg polydecanol 9-lauryl ether were added and dissolved and then mixed with the insulin solution. This mixture was then sprayed under pressure into a 1 wt. % solution of Phospholipon-H (trade mark) saturated lecithin, to form mixed micelles. This procedure gave a multilamellar, mixed amphiphile insulin solution with 50 units/mL.

The structure of the multilamellar, mixed amphiphile insulin was examined under a light microscope and the particle size was analysed by laser light scattering. The average particle size was estimated to be about 2 to 10 nm.

In one set of tests, ten healthy human volunteers were studied. The volunteers were tested with insulin, taken orally and taken by injection. The volunteers fasted from midnight prior to the test, with no food being taken during the 4 hour study.

Each of the volunteers received 10 units insulin. In one test, the oral insulin was administered with a metered dose spray. In another test, the insulin was administered by injection. Blood glucose levels, in mmol/L, were monitored every 30 minutes by Bayer's Glucometer Elite.

The average results for the ten volunteers, of the trial were as follows:

TABLE II

| Time (minutes) | Oral Insulin (10 units) | Injection (10 units) |
| --- | --- | --- |
| 0 | 5.5 | 5.3 |
| 30 | 5.0 | 5.2 |
| 60 | 4.6 | 4.2 |
| 90 | 4.2 | 3.8 |
| 120 | 4.0 | 3.6 |
| 150 | 3.6 | 3.3 |
| 180 | 3.1 | 3.0 |

The results show that the oral insulin formulation, within the scope of the present invention, at an equivalent dosage, is comparable with the injected insulin.

EXAMPLE III

To 10 mL of the insulin solution prepared in Example I, 50 mg of sodium lauryl sulphate was added and dissolved completely. This mixture was then sprayed under pressure into a 1 wt. % solution of Phospholipon-H (trade mark) saturated lecithin to form mixed micelles. This procedure gave a multilamellar, mixed amphiphile insulin solution with 50 units/mL.

This composition, which is outside the scope of the present invention, was tested on 10 healthy volunteers and compared to injected insulin, as in Example II.

The average results for the ten volunteers, of the trial were as follows:

TABLE III

| Time (minutes) | Oral Insulin (10 units) | Injection (10 units) |
| --- | --- | --- |
| 0 | 5.7 | 5.9 |
| 30 | 5.8 | 5.7 |
| 60 | 5.5 | 5.0 |
| 90 | 5.4 | 4.8 |
| 120 | 5.3 | 4.3 |
| 150 | 5.4 | 3.8 |
| 180 | 5.3 | 3.2 |

The results show that the oral insulin formulation, outside the scope of the present invention, at an equivalent dosage, had little effect. This is probably because the insulin was not absorbed, and degraded faster.

EXAMPLE IV

To 10 mL of the insulin solution prepared in Example I, 100 mg of sodium lauryl sulphate was added and dissolved completely.

This composition, which is outside the scope of the present invention, was tested on 10 healthy volunteers and compared to injected insulin, as in Example II.

The average results for the ten volunteers, of the trial were as follows:

TABLE IV

| Time (minutes) | Oral Insulin (10 units) | Injection (10 units) |
| --- | --- | --- |
| 0 | 6.1 | 5.9 |
| 30 | 6.0 | 5.7 |
| 60 | 5.8 | 5.2 |
| 90 | 5.7 | 4.7 |
| 120 | 5.6 | 4.3 |
| 150 | 5.5 | 3.7 |
| 180 | 5.6 | 3.3 |

The results show that the oral insulin formulation, outside the scope of the present invention, at an equivalent dosage, had little effect.

EXAMPLE V 10 mL of the insulin solution prepared in Example I was added to a 1 wt. % solution of Phospholipon-H saturated lecithin.

This composition, which is outside the scope of the present invention, was tested on 10 healthy volunteers and compared to injected insulin, as in Example II.

The average results for the ten volunteers, of the trial were as follows:

TABLE V

| Time (minutes) | Oral Insulin (10 units) | Injection (10 units) |
| --- | --- | --- |
| 0 | 6.2 | 5.9 |
| 30 | 6.3 | 5.6 |
| 60 | 6.2 | 5.0 |
| 90 | 6.4 | 4.6 |
| 120 | 6.5 | 4.1 |
| 150 | 6.4 | 3.8 |
| 180 | 6.5 | 3.2 |

The results show that the oral insulin formulation, outside the scope of the present invention, at an equivalent dosage, had no effect.

EXAMPLE VI

To 10 mL of the insulin solution prepared in Example I, 50 mg of sodium lauryl sulphate was added and dissolved completely. In 50 mL of water, 50 mg trihydroxy-oxo-cholanylglycine and 50 mg stearamide DEA were added and dissolved and then mixed with the insulin solution. This mixture was then sprayed under pressure into a 1 wt. % solution of sphingomyelin, to form mixed micelles. This procedure gave a mixed amphiphile insulin solution with 50 units/mL.

The structure of the mixed amphiphile insulin was examined under a light microscope and the particle size was analysed by laser light scattering.

This composition, which is within the scope of the present invention, was tested on 10 diabetic volunteers and compared to injected insulin, as in Example I.

The average results for the ten volunteers, of the trial were as follows:

TABLE VI

| Time (minutes) | Oral Insulin (10 units) | Injection (10 units) |
| --- | --- | --- |
| 0 | 7.8 | 8.0 |
| 30 | 6.5 | 7.0 |

TABLE VI-continued

| Time (minutes) | Oral Insulin (10 units) | Injection (10 units) |
| --- | --- | --- |
| 60 | 5.3 | 6.0 |
| 90 | 5.1 | 5.0 |
| 120 | 4.8 | 4.6 |
| 150 | 4.1 | 4.2 |
| 180 | 3.6 | 3.5 |

The results show that the oral insulin formulation, within the scope of the present invention, at an equivalent dosage, is comparable with the injected insulin.

EXAMPLE VII

To 10 mL of the insulin solution prepared in Example I, 100 mg of sodium lauryl sulphate was added and dissolved completely. In 50 mL of water, 100 mg sodium hyaluronate, 0.5 mL glycolic acid and 0.5 mL propylene glycol were added and dissolved and then mixed with the insulin solution. This mixture was then sprayed under pressure into a 1 wt. % solution of Phospholipon-H (trade mark) saturated lecithin, to form mixed micelles.

In one set of tests, ten healthy human volunteers were studied. The volunteers were tested with insulin, applied topically and taken by injection. The volunteers fasted from midnight prior to the test, with no food being taken during the 4 hour study.

Each of the volunteers received 10 units insulin. In one test, the insulin was administered topically to a 2 cm² area of the back of the hand. In another test, the insulin was administered by injection. Blood glucose levels, in mmol/L, were monitored every 30 minutes by Bayer's Glucometer Elite.

The average results for the ten volunteers, of the trial were as follows:

TABLE II

| Time (minutes) | Topical Insulin (10 units) | Injection (10 units) |
| --- | --- | --- |
| 0 | 5.5 | 5.3 |
| 30 | 5.3 | 5.3 |
| 60 | 5.0 | 5.0 |
| 90 | 4.9 | 4.6 |
| 120 | 4.8 | 4.3 |
| 150 | 4.7 | 4.0 |
| 180 | 4.5 | 3.8 |

The results show that the topical insulin formulation, within the scope of the present invention, at an equivalent dosage, is comparable with the injected insulin.

What is claimed is:

1. A mixed liposome pharmaceutical formulation with multilamellar vesicles, comprising a pharmaceutical agent, water, an alkali metal C8 to C22 alkyl sulphate in a concentration of from 1 to 10 wt./wt. % of the total formulation, at least one membrane-mimetic amphiphile and at least one phospholipid, wherein the membrane-mimetic amphiphile is selected from the group consisting of hyaluronic acid, pharmaceutically acceptable salts of hyaluronic acid, lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, diocta-decyldimethylammonium chloride, sulphosuccinates, stearamide DEA, gamma-linoleic acid, borage oil, evening primrose oil, monoolein, sodium tauro dihydro fusidate, fusidic acid, alkali metal isostearyl lactylates, alkaline earth metal isostearyl lactylates, panthenyl triacelate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, trihydroxy-oxo-cholanylglycine and alkali metal salts thereof, and octylphenoxypolythoxyethanol, polydecanol X-lauryl ether, polydecanol X-oleyl ether, wherein X is from 9 to 20, and combinations thereof, and wherein the phospholipid is selected from the group consisting of phospholipid GLA, phosphatidyl serine, phosphatidylethanolamine, inositolphosphatides, dioleoylphosphatidylethanolamine, sphingomyelin, ceramides, cephalin, triolein, lecithin, saturated lecithin and lysolecithin, and combinations thereof, and wherein each membrane mimetic amphiphile and phospholipid is present in a concentration of from 1 to 10 wt./wt. % of the total formulation, and the total concentration of membrane mimetic amphiphiles and phospholipids is less than 50 wt./wt. % of the formulation.

2. A formulation according to claim 1 wherein the alkali metal C8 to C22 alkyl sulphate is sodium lauryl sulphate.

3. A formulation according to claim 1 wherein there are at least two membrane mimetic amphiphiles.

4. A formulation according to claim 1 wherein the membrane-mimetic amphiphile is selected from the group consisting of hyaluronic acid, pharmaceutically acceptable salts of hyaluronic acid and mixtures thereof, the concentration of said amphiphile being from about 1 to about 5 wt./wt. %.

5. A formulation according to claim 1 which contains sodium lauryl sulphate and combinations selected from the group consisting of:

i) sodium salt of trihydroxy-oxo-cholanyl glycine, sphingomyelin and stearamide DEA;

ii) sodium salt of trihydroxy-oxo-cholanyl glycine and phospholipid GLA;

iii) phospholipid GLA, polydecanol 9-lauryl ether and octylphenoxyethoxyethanol;

iv) ceramide and stearamidopropyl phosphatidyl PG-diammonium chloride;

v) borage amidopropyl phosphatidyl PG-diammonium chloride and lecithin;

vi) octylphenoxypolyethoxyethanol and saturated lecithin;

vii) lecithin, evening primrose oil and trihydroxy-oxo-cholanylglycine;

viii) sodium hyaluronate, trihydroxy oxo-cholanylglycine, lecithin and evening of primrose oil;

ix) sodium hyaluronate, saturated lecithin, and evening primrose oil;

x) sodium hyaluronate and saturated lecithin; and xi) sodium hyaluronate and sphingomyelin.

6. A formulation according to claim 1 wherein the pharmaceutical agent is selected from the group consisting of insulin, heparin, hirugen, hirulos, hirudine, interferons, interleukins, cytokines, mono and polyclonal antibodies, chemotherapeutic agents, vaccines, glycoproteins, hormones, bacterial toxoids, calcitonins, insulin like growth factors (IGF), glucagon like peptides (GLP-1 or GLP-2), steroids, retinoids, antibiotics, thrombolytic compounds, platelet inhibitors, DNA, gene therapeutics, RNA and antisense oligonucleotides.

7. A process for making a pharmaceutical composition comprising: mixing in a high shear mixer a pharmaceutical agent, water, an alkali metal C8 to C22 alkyl sulphate in a concentration of from 1 to 10 wt./wt. % of the total formulation, at least one membrane-mimetic amphiphile and at least one phospholipid, wherein the membrane-mimetic amphiphile is selected from the group consisting of hyaluronic acid, pharmaceutically acceptable salts of hyaluronic acid, lauramidopropyl betain, lauramide monoisopropanolamide, sodium cocoamphopropionate, bishydroxypropyl dihydroxpropyl stearammonium chloride, polyoxyethylene dihydroxypropyl stearammonium chloride, dioctadecyldimethylammonium chloride, sulphosuccinates, stearamide DEA, gamma-linoleic acid, borage oil, evening primrose oil, monoolein, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, trihydroxy-oxo-cholanylglycine and alkali metal salts thereof, and octylphenoxypolythoxyethanol, polydecanol X-lauryl ether and polydecanol X-oleyl ether, wherein X is from 9 to 20, and wherein the phospholipid is selected from the group consisting of phospholipid GLA, phosphatidyl serine, phosphatidylethanolamine, inositolphosphatides, dioleoylphosphatidylethanolamine, sphingomyelin, ceramides, cephalin, triolein, lecithin, saturated lecithin and lysolecithin, and wherein each membrane mimetic amphiphile and phospholipid is present in a concentration of from 1 to 10 wt./wt. % of the total formulation, and the total concentration of membrane mimetic amphiphiles and phospholipids is less than 50 wt./wt. % of the formulation;

said mixing being continued until the composition is in multilamellar vesicle form.

8. A process according to claim 7 wherein the membrane-mimetic amphiphile is selected from the group consisting of hyaluronic acid, pharmaceutically acceptable salts of hyaluronic acid and mixtures thereof, the concentration being from about 1 to about 5 wt./wt. %.

9. A process according to claim 7 wherein the alkali metal C8 to C22 alkyl sulphate is sodium lauryl sulphate.

10. A process according to claim 7 wherein phospholipids and amphiphiles comprise a combination selected from the group consisting of:

i) sodium salt of trihydroxy-oxocholanyl glycine, sphingomyelin and stearamide DEA;

ii) sodium salt of trihydroxy-oxo-cholanyl glycine and phospholipid GLA;

iii) phospholipid GLA, polydecanol 9-lauryl ether and octylphenoxyethoxyethanol;

iv) ceramide and stearamidopropyl phosphatidyl PG-diammonium chloride;

v) borage amidopropyl phophatidyl PG-diammonium chloride and lecithin;

vi) octylphenoxyethoxyethanol and saturated lecithin;

vii) lecithin, evening primrose oil and trihydroxy-oxocholanyl glycine;

viii) sodium hyaluronate, trihydroxy-oxo-cholanyl glycine, lecithin and evening of primrose oil;

ix) saturated lecithin, sodium hyaluronate and evening primrose oil;

x) saturated lecithin and sodium hyaluronate; and xi) sodium hyaluronate and sphingomyelin.

11. A process according to claim 7 wherein the pharmaceutical agent is selected from the group consisting of insulin, heparin, hirugen, hirulos, hirudine, interferons, interleukins, cytokines, mono and polyclonal antibodies, chemotherapeutic agents, vaccines, glycoproteins, bacterial toxoids, hormones, calcitonins, insulin like growth factors (IGF), glucagon like peptides (GLP-1 or GLP-2), antibiotics, thrombolytic compounds, platelet inhibitors, DNA, RNA, gene therapeutics and antisense oligonucleotides.

12. A process according to claim 7 wherein the method of mixing is a high turbulence or high shear method of mixing.

13. A process according to claim 12 selected from the group consisting of i) injecting the phospholipid, in liquid form, at high velocity through at least one nozzle into an aqueous phase of the membrane-mimetic amphiphile, ii) injecting the membrane-mimetic amphiphile, in liquid form, at high velocity through at least one nozzle into an aqueous phase of the phospholipid, and iii) injecting the phospholipid, in liquid form, at high velocity through at least one nozzle and the membrane mimetic amphiphile, in liquid form, at high velocity through at least one nozzle into a mixing chamber; and wherein the alkali metal C8 to C22 alkyl sulphate is present with either the phospholipid or membrane-mimetic amphiphile.

14. A process according to claim 13 wherein the velocity the phospholipid and amphiphile liquids is from 0 to 15 m/s through 0.5 to 1.0 mm diameter nozzle apertures.

15. A process according to claim 12 wherein the ratio of the membrane-mimetic amphiphile aqueous solution to the phospholipid solution is about 5:1 to about 20:1.

16. A process according to claim 13 wherein the ratio of the membrane-mimetic amphiphile aqueous solution to the phospholipid solution is about 5:1 to about 20:1.

17. A pressurized container containing a propellant which is liquid under pressure and an intermediate mixed liposome formulation which comprises:

i) a pharmaceutical agent, ii) water, iii) an alkali metal C8 to C22 alkyl sulphate in a concentration of from 1 to 10 wt./wt. % of the total formulation. iv) at least one membrane-mimetic amphiphile and at least one phospholipid, wherein the membrane-mimetic amphiphile is selected from the group consisting of hyaluronic acid, pharmaceutically acceptable salts of hyaluronic acid, lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, gamma-linoleic acid, borage oil, evening primrose oil, monoolein, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, trihydroxy-oxo-cholanylglycine and alkali metal salts thereof, and octylphenoxypolythoxyethanol, polydecanol X-lauryl ether, polydecanol X-oleyl ether, wherein X is from 9 to 20, and combinations thereof, and wherein the phospholipid is selected from the group consisting of phospholipid GLA, phosphatidyl serine, phosphatidylethanolamine, inositolphosphatides, dioleoylphosphatidylethanolamine, sphingomyelin, ceramides, cephalin, triolein, lecithin, saturated lecithin and lysolecithin, and combinations thereof, and wherein each membrane mimetic amphiphile and phospholipid is present in a concentration of from 1 to 10 wt./wt. % of the total formulation, and the total concentration of membrane mimetic amphiphiles and phospholipids is less than 50 wt./wt. % of the formulation, and v) a phenolic compound selected from the group consisting of phenol and methyl phenol in a concentration of from 1 to 10 wt./wt. % of the total formulation.

18. A container according to claim 17 wherein the propellant is selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof.

19. A container according to claim 18 wherein the intermediate formulation also contains a compound selected from glycerin, polyglycerin and mixtures thereof in an amount of from 1–40 wt./wt. % of the intermediate formulation.

20. A container according to claim 18 wherein the weight ratio of intermediate formulation to propellant is from 5:95 to 25:75.

21. A container according to claim 18 wherein the alkali metal C8 to C22 alkyl sulphate is sodium lauryl sulphate.

22. A container according to claim 18 wherein the propellant is selected from the group consisting of tetrafluoroethane, tetrafluoropropane, dimethylfluoropropane, heptafluoropropane, dimethyl ether, n-butane and isobutane.

23. A container according to claim 17 wherein the pharmaceutical agent is selected from the group consisting of insulin, heparin, hirugen, hirulos, hirudine, interferons, interleukins, cytokines, mono and polyclonal antibodies, chemotherapeutic agents, vaccines, glycoproteins, bacterial toxoids, hormones, calcitonins, insulin like growth factors (IGF), glucagon like peptides (GLP-1 or GLP-2), antibiotics, thrombolytic compounds, platelet inhibitors, DNA, RNA, gene therapeutics and antisense oligonucleotides.

24. A container according to claim 17 wherein the pharmaceutical agent is insulin.

25. A container according to claim 17 wherein container is a metered dose aerosol dispenser.

26. A method for administering aerosol pharmaceutical compositions of the present invention, by spraying a predetermined amount of a mixture of a propellant and an intermediate mixed liposome formulation which comprises:

i) a pharmaceutical agent,
ii) water,
iii) an alkali metal C8 to C22 alkyl sulphate in a concentration of from 1 to 10 wt./wt. % of the total formulation,
iv) at least one membrane-mimetic amphiphile and at least one phospholipid, wherein the membrane-mimetic amphiphile is selected from the group consisting of hyaluronic acid, pharmaceutically acceptable salts of hyaluronic acid, lauramidopropyl betain, lauramide monoisopropanolamide, sodium cocoamphopropionate, bishydroxypropyl dihydroxypropyl stearammonium chloride, polyoxyethylene dihydroxypropyl stearammonium chloride, dioctadecyldimethylammonium chloride, sulphosuccinates, stearamide DEA, gamma-linoleic acid, borage oil, evening primrose oil, monoolein, sodium tauro dihydro fusidate, fusidic acid, alkali metal isostearyl lactylates, alkaline earth metal isostearyl lactylates, panthenyl triacetate, cocamidopropyl phosphatidyl PG-diammonium chloride, stearamidopropyl phosphatidyl PG-diammonium chloride, borage amidopropyl phosphatidyl PG-diammonium chloride, borage amidopropyl phosphatidylcholine, polysiloxy pyrrolidone linoleyl phospholipid, trihydroxy-oxo-cholanylglycine and alkali metal salts thereof, and octylphenoxypolythoxyethanol, polydecanol X-lauryl ether, polydecanol X-oleyl ether, wherein X is from 9 to 20, and combinations thereof, and wherein the phospholipid is selected from the group consisting of phospholipid GLA, phosphatidyl serine, phosphatidylethanolamine, inositolphosphatides, dioleoylphosphatidylethanolamine, sphingomyelin, ceramides, cephalin, triolein, lecithin, saturated lecithin and lysolecithin, and combinations thereof, and wherein each membrane mimetic amphiphile and phospholipid is present in a concentration of from 1 to 10 wt./wt. % of the total formulation, and the total concentration of membrane mimetic amphiphiles and phospholipids is less than 50 wt./wt. % of the formulation, and v) a phenolic compound selected from the group consisting of phenol and methyl phenol in a concentration of from 1 to 10 wt./wt. % of the total formulation.

27. A method according to claim 26 wherein the mixture is administered from a metered dose dispenser.

28. A method according to claim 27 wherein the propellant is selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof.

29. A method according to claim 28 wherein the intermediate formulation also contains a compound selected from glycerin, polyglycerin and mixtures thereof in an amount of from 1–40 wt./wt. % of the intermediate formulation.

30. A method according to claim 28 wherein the pharmaceutical agent is selected from the group consisting of insulin, heparin, hirugen, hirulos, hirudine, interferons, interleukins, cytokines, mono and polyclonal antibodies, chemotherapeutic agents, vaccines, glycoproteins, bacterial toxoids, hormones, calcitonins, insulin like growth factors (IGF), glucagon like peptides (GLP-1 or GLP-2), antibiotics, thrombolytic compounds, platelet inhibitors, DNA, RNA, gene therapeutics and antisense oligonucleotides.

31. A method according to claim 28 wherein the pharmaceutical agent is insulin.

32. A method according to claim 28 wherein the mixture is sprayed into the buccal cavity of a human being, without inhalation.

33. A method according to claim 30 wherein the mixture is sprayed into the buccal cavity of a human being, without inhalation.

34. A method according to claim 31 wherein the mixture is sprayed into the buccal cavity of a human being, without inhalation.

* * * * *